(12) United States Patent
Rabin

(10) Patent No.: US 6,284,942 B1
(45) Date of Patent: Sep. 4, 2001

(54) CONFIDENCE BUILDING INCONTINENCE PAD

(75) Inventor: Jill Rabin, New York, NY (US)

(73) Assignee: Long Island Jewish Medical Center, New Hyde Park, NY (US)

( * ) Notice: Subject to any disclaimer, the term of this patent is extended or adjusted under 35 U.S.C. 154(b) by 0 days.

(21) Appl. No.: 09/072,107

(22) Filed: May 4, 1998

(51) Int. Cl.[7] .................................................. A61F 13/15
(52) U.S. Cl. .................... 604/361; 604/385.01; 604/378
(58) Field of Search ............................. 422/56; 604/361, 604/368, 383, 362, 378, 385.01; 428/35.7

(56) References Cited

U.S. PATENT DOCUMENTS

| | | |
|---|---|---|
| 3,675,654 | 7/1972 | Baker et al. . |
| 3,952,746 | 4/1976 | Summers . |
| 4,231,370 | 11/1980 | Mroz et al. . |
| 4,287,153 * | 9/1981 | Towsend ................................ 422/56 |
| 4,327,731 | 5/1982 | Powell . |
| 4,507,121 * | 3/1985 | Leung ................................ 604/361 |
| 4,568,341 * | 2/1986 | Mitchell et al. ...................... 604/368 |
| 4,738,674 | 4/1988 | Todd et al. . |
| 4,931,051 | 6/1990 | Castello . |
| 4,994,037 * | 2/1991 | Bernardin ............................ 604/368 |
| 5,167,652 * | 12/1992 | Mueller .............................. 604/385.1 |
| 5,290,269 * | 3/1994 | Heiman ................................ 604/378 |
| 5,354,289 * | 10/1994 | Mitchell et al. ..................... 604/361 |
| 5,766,212 * | 6/1998 | Jitoe et al. .......................... 604/361 |
| 5,851,611 * | 12/1998 | Guttag ................................ 428/35.7 |
| 5,855,571 * | 1/1999 | Steger et al. ........................ 604/368 |
| 5,879,344 * | 3/1999 | Koczab ................................ 604/383 |

* cited by examiner

Primary Examiner—John G. Weiss
Assistant Examiner—Jacqueline F Stephens
(74) Attorney, Agent, or Firm—Amster, Rothstein & Ebenstein

(57) ABSTRACT

A pad which permits a quantitative estimate of urinary incontinence includes three zones: a core zone having a defined urine absorption capacity and undergoing a first color change as it becomes wetted with urine; an inner zone having a urine absorption capacity greater than the capacity of the core zone and undergoing a second color change when it becomes wetted with urine; and an outer zone having a urine absorption capacity greater than the capacity of the inner zone and undergoing a third color change when it becomes wetted with urine. Each of the first, second and third color changes is visually distinct. The inner zone is concentrically disposed about the core zone, and the outer zone is concentrically disposed about the inner zone; alternatively, the inner zone is disposed at one end of the core zone, and the outer zone is disposed at the other end of the core zone.

29 Claims, 2 Drawing Sheets

CONFIDENCE BUILDING INCONTINENCE PAD

BACKGROUND OF THE INVENTION

The present invention relates to a urinary incontinence pad, and more particularly to such a pad which is designed to instill confidence in a female wearer.

A conventional incontinence pad is designed to prevent embarrassment to the wearer resulting from her urinary incontinence. Briefly, the incontinence pad absorbs the urine or otherwise prevents the urine from becoming visible on the clothing worn by the user. Nonetheless, wearers of the conventional incontinence pad are often afraid to leave the house for fear that the urinary incontinence may occur and the discharged urine not be sufficiently captured by the incontinence pad. This partially results from the fact that the typical user of the conventional incontinence pad is uncertain as to how much and where urinary leakage typically occurs, only the roughest measure of the amount and location of urinary leakage being determinable by the user from the wet feel and look of the worn incontinence pad.

It would be desirable for a patient to gain control over her urinary incontinence problem through a special incontinence pad that permits the patient to assess the amount and location of urine leakage. This would enable the patient to monitor her progress on various therapeutic modalities, such as timed voiding or fluid-volume intake, medication, surgery (post-operative) or physical therapeutic techniques. Thus, a patient can be an active partner in treating her incontinence problem and hopefully achieve a greater degree of confidence as she becomes more familiar with her particular incontinence problem.

Accordingly, it is an object of the present invention to provide a urinary incontinence pad which enables the patient to determine the amount and location of urine leakage.

Another object is to provide such a pad which assists a patient to gain control over her urinary incontinence problem and develop confidence.

SUMMARY OF THE INVENTION

It has now been found that the above-identified objects of the present invention are obtained in a pad which permits a quantitative estimate of urinary incontinence. The pad comprises three zones as follows: a first or core zone having a defined urine absorption capacity and undergoing a first color change as it becomes wetted with urine; a second or inner zone having a urine absorption capacity greater than the capacity of the core zone and undergoing a second color change when it becomes wetted with urine; and a third or outer zone having a urine absorption capacity greater than the capacity of the inner zone and undergoing a third color change when it becomes wetted with urine. Each of the first, second and third color changes is visually distinct.

Preferably, the core zone is centrally disposed, the inner zone is concentrically disposed about the core zone, and the outer zone is concentrically disposed about the inner zone. Alternatively, the inner zone is disposed at one end of the core zone (preferably the rear) and the outer zone is disposed at the other end of the core zone (preferably the front). The core zone is typically configured and dimensioned to cover a urethral meatus.

In a preferred embodiment, the first color change is both qualitative and quantitative, and the outer zone has a relative high urine absorption characteristic relative to the core zone and the inner zone. Preferably, the core zone includes an enzymatic moisture indicator, and the core zone color change is from yellow through light green to deep turquoise. The inner zone includes a hydratable salt moisture indicator, and the inner zone color change is from a colorless white to blue. The outer zone includes a capillary action moisture indicator, and the outer zone color change is from white to red. Preferably, the core zone urine absorption capacity is 0–20 cc of urine, the inner zone urine absorption capacity is 20–100 cc of urine, and the outer zone urine absorption capacity is greater than 100 cc of urine.

In another preferred embodiment, the pad includes a first layer of wicking material, a second layer of absorbent material disposed over the first layer, and a third layer of moisture-impervious material disposed over the second layer. The core zone, inner zone, and outer zone are in the second or absorbent layer. Wicking portions of the first layer extend to each of the zones. The pad may optionally include means for precluding urine transfer between the zones so that each zone receives only the wicked moisture.

In yet another preferred embodiment, the pad comprises at least two urine absorption zones: a first zone having a first urine absorption capacity and undergoing a first color change as it becomes progressively wetter with urine, and a second zone having a greater urine absorption capacity than the first absorption urine capacity and undergoing a second color change when it becomes saturated with urine. The first and second color changes are visually distinct.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
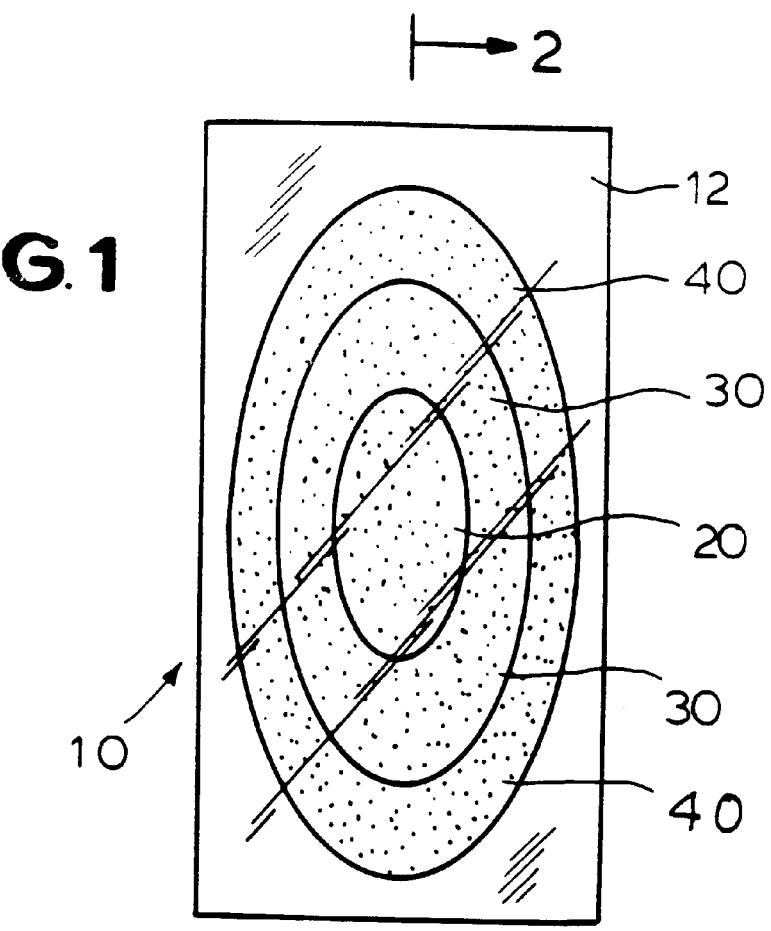
FIG. 1 is a front elevational view of a first embodiment of an incontinence pad according to the present invention.
Figure 2:
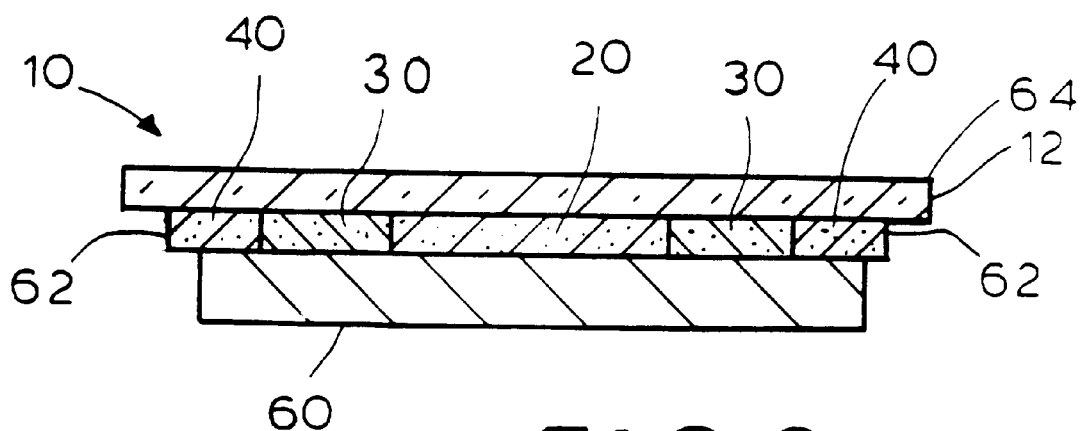
FIG. 2 is a sectional view thereof taken along the line 2—2 of FIG. 1.

Referring now to the drawing, and in particular to FIGS. 1 and 2, therein illustrated is a first embodiment of an incontinence pad according to the present invention, generally designated by the reference numeral 10. The pad 10 is preferably designed for wear by a female (as opposed to a male), and optimally for a human female. The pad 10 is preferably soft, elongated and elliptical, varying in dimensions and configuration based upon the size chosen. Preferably, the pad will be available in various absorbencies, such as light, moderate and heavy. Typically, the length will be about three times the width, and the depth will be about 10% of the length. The pad will allow full absorption of urinary leakage up to 200 cc of urine (including the urine absorbed in each of the zones 20, 30, 40). When the pad is dry, the zones thereof will preferably be invisible to the naked eye (i.e., colorless, white (like the typical pad body) or pale yellow) or, alternatively, include only zone outlines.

The pad 10 includes a body 12 which is divided into three zones as follows:

(A) The core zone 20 has a defined urine absorption capacity and undergoes a first color change as it becomes wetted with urine. The core zone 20 is adapted to be placed over the urethral meatus. The urine absorption capacity for the core zone is preferably 0–20 cc of urine, and it preferably undergoes at least a two-phase color change as it becomes progressively wetter with urine. Preferably the core zone 20 includes an enzymatic moisture indicator 22 which undergoes a color change from yellow (from light yellow to dark yellow) through light green to deep turquoise. Thus, the core zone color change is both qualitative and quantitative since the user can judge from the color after use roughly how much urine was discharged.

(B) The inner zone 30 has a urine absorption capacity greater than the capacity of the core zone 20 and undergoes a second color change e when it becomes wetted with urine. Preferably, the urine absorption capacity of the inner zone 30 is 20–100 cc of urine, and it undergoes the second color change when it becomes saturated with urine. Preferably, the inner zone 30 includes a hydratable salt moisture indicator 32 which undergoes a color change from colorless or white to blue.

(C) The outer zone 40 has a urine absorption capacity greater than the capacity of the inner zone 30 and undergoes a third color change when it becomes wetted with urine. Preferably, the urine absorption capacity of the outer zone 40 is at least 100 cc of urine, and it undergoes a third color change when it becomes saturated with urine. Preferably, the outer zone 40 includes a capillary action moisture indicator which undergoes a color change from white to red.

As will be appreciated by those skilled in the art, the pad may comprise more than three zones, with the color change in each zone being visually distinct. While the preferred embodiment utilizes in the core zone an enzymatic moisture indicator which undergoes a color change from yellow through light green to deep turquoise, in the inner zone a hydratable salt moisture indicator which undergoes a color change from colorless or white to blue, and in the outer zone a capillary moisture indicator which undergoes a color change from white to red, clearly the same or different types of indicators may be used.

A suitable enzymatic moisture indicator 22 is described in U.S. Pat. No. 4,327,731. This indicator 22 is preferred for use in the core zone 20 because it has both a qualitative and quantitative feature—that is, not only is there a color change with any urine, but there is a progressive color change with the amount of urine. The first color change would range from yellow (with a light yellow for no leakage and a dark yellow for minor leakage) to light green (with a substantial amount of leakage) to deep blue or turquoise (with the highest amount of leakage). The quantitative feature is especially critical in the core zone 20 since the user is typically interested in learning first whether there was any urine leakage, and then whether it was a large or small amount of leakage. As the amount of urine leakage is higher in the inner and outer zones 30, 40, the patient has less interest in learning the exact amount of urine leakage. Thus, while the pad 10 is designed for patients with all levels of urinary leakage, the qualitative and quantitative feature of the core zone 20 enables patients with very little urinary leakage to be more confident and, perhaps, eventually to become entirely dry. Because the patient can monitor her own urinary leakage, she develops confidence in her ability to predict leakage and is encouraged to participate in her own treatment program.

The enzymatic reaction occurs when varying amounts of urine produce varying amounts of glucose in the dry substrate, thereby causing the color change from yellow through light green to deep turquoise, as noted above. The "Test-Tape" system uses orthotolidine as the oxidizable chromogen which detects glucose in urine, the color change depending on the amount of glucose detected. The amount of glucose in the urine would be dependent not only upon the amount of glucose in a particular patient's urine, but also upon the amount of urine leakage and, therefore, would produce varying concentrations of visible pigment to provide a semi-quantifiable urine leakage indicator system.

A suitable hydratable salt moisture indicator 32 is described in U.S. Pat. No. 4,931,051. This indicator 32 has the characteristic of changing the color it exhibits in its normal and anhydrous state to a contrasting color when it becomes hydrated. The hydratable salt 32 is preferably a copper sulfate salt, which is white in the anhydrous state and deep blue in the hydrated state. Other preferred hydratable salt indicators include cobalt, nitrate, ferrous or ferric salt, each of which changes from colorless or white to blue as it becomes hydrated. A binder may be used for the hydratable salt to reduce its toxicity and prevent contact of the hydratable salt with the wearer.

The hydratable salt moisture indicator 32 is basically qualitative, and quantitative only in terms of the degree of shading of the color. Assuming that the urinary leakage reaching the inner zone is 20–100 cc, the moisture indicator might be a light shade of blue if the leakage was only 20 cc, and the deepest shade of blue if it was at least 100 cc. Thus it will be appreciated that the hydratable salt urine indicator 32 is substantially less quantitative than the enzymatic moisture indicator 22 and requires saturation of the zone to cause the full color change.

Strings or wicks of the hydratable salt moisture indicator are impregnated onto a water-soluble binder of polyethylene glycol, either in string form, linear string form along the surface of the core zone, or on an actual paper layer contained either within the absorbent layer or between the absorbent and outer liner layers. The water content of the urine released during incontinence would activate the color change of the hydratable salt. The paper itself or the wicks could be coated with polypropylene so as to reduce the toxicity of the hydratable salt urine indicator. The indicator is safe and non-toxic, especially if the hydratable salt is coated with polypropylene. The color change is drastic and non-ambiguous. The indicator can tolerate normal perspiration by the wearer without a color change since it takes at least 20 cc to effect a color change.

A suitable capillary action moisture , indicator 42 is described in U.S. Pat. No. 4,738,674. The capillary action moisture indicator technology is preferred for the outer zone 40 as it helps the absorbent layer with the additional urine loss after saturation of the core and inner zones, with anything over 100 cc of urine being immediately brought by capillary action into the outer zone 40. Typically 100 cc of urine or saturation of the zone would be the minimum amount of urine required to initiate the color change from white to red.

The capillary action moisture indicator is preferably non-toxic, utilizing, for example, one of the water-soluble dies described in U.S. Pat. No. 3,675,654. The water-soluble die may be mixed with a masking agent, such as talc, and impregnated onto wicks or strings lining the absorbent layer of the pad so that moisture (urine) is wicked into the outer zone to produce a color change. Litmus paper or food coloring may be used as the humidity indicator paper and deployed as the wicks or impregnated onto the wicks in the outer zone, as described by U.S. Pat. No. 3,952,746. The shades of the color change in the outer zone may indicate roughly the degree of urine leakage. It will be appreciated by those skilled in the art that each of these patents describes a non-toxic technology.

It will be appreciated that other technologies may be used in the various indicators. For example, the technology in U.S. Pat. No. 4,231,370 produces a color change dependent upon a change in pH. Reliance on pH changes is not preferred, however, since the pH of urine can vary tremendously and the color change may require an extended period of time to develop, up to ten minutes.

Depending upon the construction of the pad body 12, there may or may not be any overflow of urine from the core zone 20 to the inner zone 30 and/or from the inner zone 30 to the outer zone 40. It will be appreciated, however, that, if desired, urine transfer directly from one zone to another core to inner and inner to outer may be enabled. In both cases, the inner and outer zones 30 and 40 would become wet and change color only when there was substantially greater urine leakage than that absorbable by the core zone 20.

Preferably the color changes of the three indicators 22, 32, 42 in the three zones 20, 30, 40 are visually distinct. As described above for the preferred embodiment, the core zone color changes from yellow through light green to deep turquoise, the inner zone change is from colorless or white to blue, and the outer zone color change is from white to red. These color changes are not only visually distinct, but involve contrasting colors and are thus easily readable by a user.

Preferably the structure of the pad 10 includes a first layer of wicking material 60 for disposition next to the body of the wearer, a second layer of absorbent material 62 disposed over the first layer of wicking material 60, and a third layer of moisture-impervious material 64 disposed over the second layer of absorbent material 62. The absorbent layer 62 may include each of the three indicators 22, 32, and 42, although the indicators may be disposed somewhat to one or another side of the absorbent layer that is, between the wicking first layer 60 and the absorbent second layer 62, or between the absorbent second layer 62 and the moisture-impervious third layer 64. Optimum placement of each indicator will depend in part on the nature and composition of the indicator. Accordingly, it is not deemed necessary to go into any further detail herein regarding the location of the indicators 22, 32, 42 among the layers 62–64.

Clearly at least one of the first and third layers 60, 64 must be transparent or translucent in order to enable viewing of the color changes occurring when urinary leakage is detected. Again, depending upon the placement of the indicators, it may be desirable for the second layer 62 to also be transparent or translucent.

It will be appreciated that the wicking layer 60 divides the total urinary discharge into three aliquots such that each of the three zones 20, 30, 40 receives one third of the discharge. Accordingly, assuming there is no moisture transfer from one zone to another, a discharge of, for example, 30 cc of urine will be seen by each zone only as a discharge of 10 cc of urine, enough to effect a color change in the core zone 20 but not in the inner or outer zones 30, 40.

In embodiment 10, the core zone 20 is encircled by the inner zone 30, and the inner zone 30 is encircled by the outer zone 40. Preferably the various zones 20, 30, 40 in the first embodiment are coaxial, with the outer zone 40 optionally extending out to the entire margin or circumference of the pad body 12.

The pad body 12 is configured and dimensioned so that the core zone 20 is disposed over the urethral meatus when the pad is being worn. In use, a patient leaking a small amount of urine will see a light color change in the core zone 20 while someone with a little more urinary leakage will see a greater color change in the same zone 20. A patient with moderate leakage would also see a dark color change in the inner zone 30. A patient with the most severe leakage would also see a dark color change in the outer zone 40. Because the wearer can thus determine generally the amount of leakage which has occurred over a given period of time, she may actually enter such information into a computerized or written log to enable her to track her progress according to a prescribed treatment regimen.

In the first embodiment 10 the three zones 20, 30, 40 are illustrated as being contiguous, with the inner zone 30 being in physical contact with the outer zone 40 and the core zone 20. However, if desired, the inner zone 20 may be spaced radially from both the core zone 20 and the outer zone 40.

Figure 3:
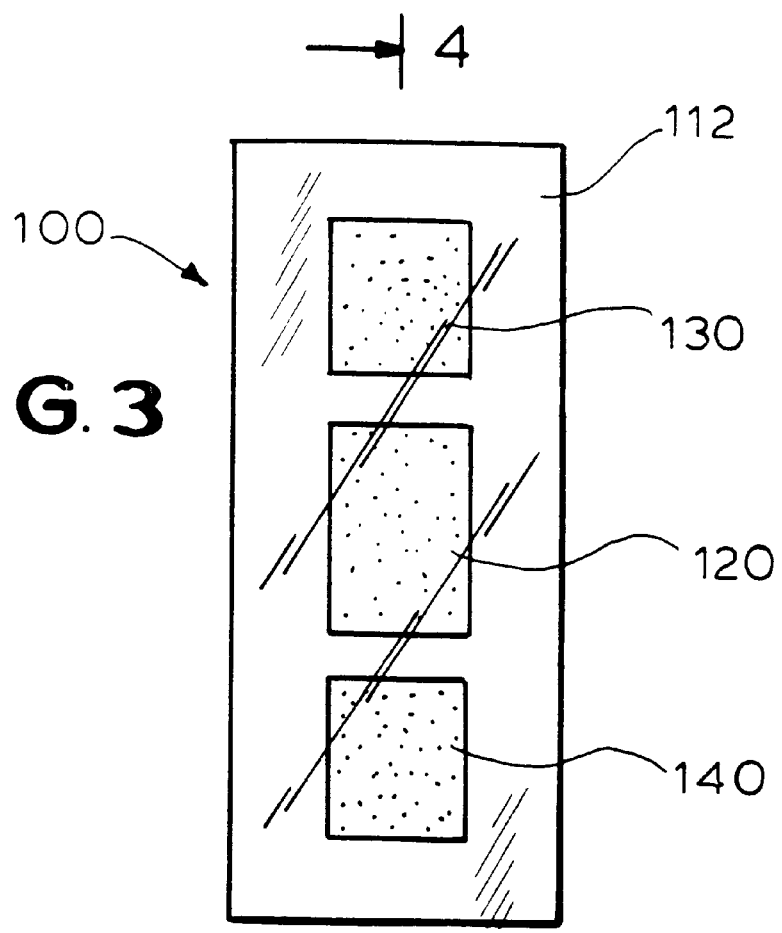
FIG. 3 is a front elevational view of a second embodiment of an incontinence pad according to the present invention.
Figure 4:
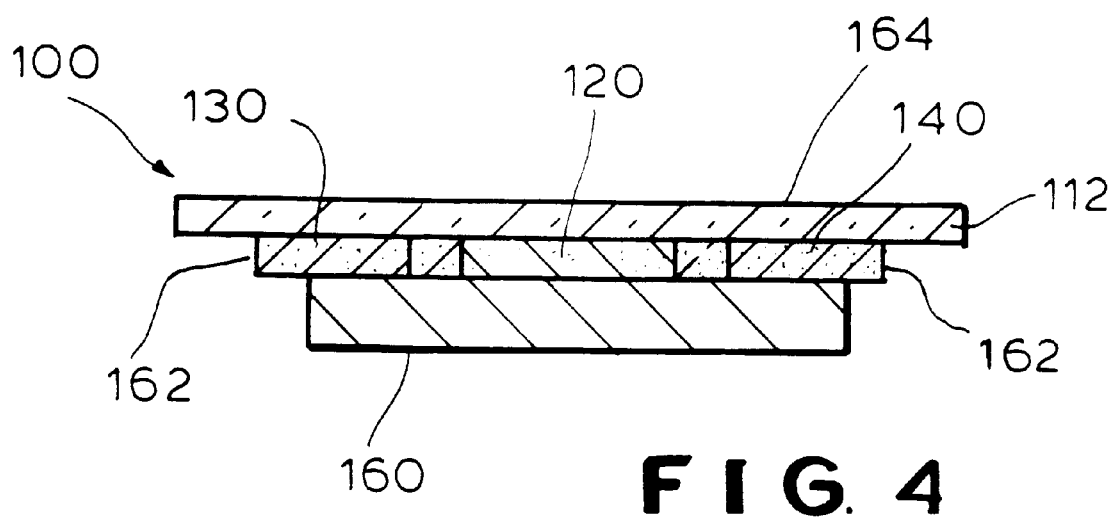
FIG. 4 is a sectional view thereof taken along the line 4—4 of FIG. 3.

Referring now to FIGS. 3 and 4, therein illustrated is a second embodiment of the present invention, generally designated by the reference numeral 100 (with each component thereof being indicated with a corresponding number of the first embodiment, but in the 100 series).

In the second or linear embodiment 100, the core zone 120 is longitudinally spaced from both the inner zone 130 and the outer zone 140. However the three zones 120, 130 and 140 may be contiguous, with the core zone 120 being in contact with the inner zone 130 (e.g., in the front thereof) and the outer zone 140 (e.g., in the rear thereof).

The concentric or coaxial system of the system embodiment 10 gives a more easily comprehended visual picture of the urine leakage than the linear system of the second embodiment 100 and is therefore preferred. Its accuracy is also less dependent on pad position.

The present invention also encompasses a confidence pad 10, 100 for a female enabling a quantitative estimate of urinary incontinence, the pad comprising at least two urine absorption zones. The first zone 20, 120 has a first urine absorption capacity and undergoes a first color change as it becomes progressively wetter with urine; the second zone 30, 130 has a greater urine absorption capacity than that of the first zone 20, 120 and undergoes a second color change when it becomes saturated with urine. The first and second color changes are visually distinct.

To summarize, the present invention provides a urinary incontinence pad which enables a patient to determine the amount and location of urine leakage, thereby assisting the patient to gain control over her urinary incontinence problem and thus develop confidence.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. An absorbent pad which permits a quantitative estimate of a single episode of urinary incontinence, said pad being urine absorbent and comprising:

(A) a first zone having a defined urine absorption capacity and undergoing a first color change as it becomes wetted with urine;

(B) a second zone having a urine absorption capacity greater than the capacity of said first zone and undergoing a second color change when it becomes wetted with urine; and (C) a third zone having a urine absorption capacity greater than the capacity of said second zone and undergoing a third color change when it becomes wetted with urine;

each of said first, second and third color changes being visible at the respective one of said zones, visually distinct, and a function of the quantity of urine absorption in said one zone.

2. The pad of claim 1 wherein said first zone is centrally disposed, said second zone is concentrically disposed about said first zone, and said third zone is concentrically disposed about said second zone.

3. The pad of claim 1 wherein said second zone is disposed adjacent one end of said first zone, and said third zone is disposed at the other end of said first zone.

4. The pad of claim 3 wherein said second zone is disposed at the rear of said first zone, and said third zone is disposed at the front of said second zone.

5. The pad of claim 1 wherein said first color change is both qualitative and quantitative.

6. The pad of claim 1 wherein said first zone includes an enzymatic moisture indicator.

7. The pad of claim 6 wherein said first zone color change is from yellow through light green to deep turquoise.

8. The pad of claim 1 wherein said second zone includes a hydratable salt moisture indicator.

9. The pad of claim 8 wherein said second zone color change is from a colorless white to blue.

10. The pad of claim 1 wherein said third zone includes a capillary action moisture indicator.

11. The pad of claim 10 wherein said third zone color change is from white to red.

12. The pad of claim 1 wherein said third zone has a relative high urine absorption characteristic relative to said first zone and said second zone.

13. The pad of claim 1 wherein said first zone urine absorption capacity is 0–20 cc of urine, said second zone urine absorption capacity is 20–100 cc of urine, and said third zone urine absorption capacity is greater than 100 cc of urine.

14. The pad of claim 1 wherein said pad includes a first layer of wicking material, a second layer of absorbent material disposed over said first layer, and a third layer of moisture-impervious material disposed over said second layer.

15. The pad of claim 14 wherein said first zone, said second zone, and said third zone are in said second layer.

16. The pad of claim 15 wherein portions of said first layer extend to each of said zones of said second layer.

17. The pad of claim 16 further including means for precluding urine transfer between said zones.

18. The pad of claim 1 wherein said first zone includes an enzymatic moisture indicator, said second zone includes a hydratable salt, and said third zone includes a capillary action moisture indicator.

19. The pad of claim 1 wherein said first zone color change is from yellow through light green to deep turquoise, said second zone color change is from a colorless white to blue, and said third zone color change is from white to red.

20. The pad of claim 1 wherein at least one of said color changes is both qualitative and quantitative, and said third zone has a relative high urine absorption characteristic relative to said first zone and said second zone.

21. The pad of claim 1 wherein said pad includes a first layer of a wicking material, a second layer of absorbent material disposed over said first layer, and a third layer of moisture-impervious material disposed over said second layer, said first zone, said second zone, and said third zone being in said second layer.

22. A confidence pad for a female enabling a quantitative estimate of a simple episode of urinary incontinence, comprising a urine-absorbent pad having at least three urine absorption zones as follows:

(A) a core zone having a urine absorption capacity of 0–20 cc of urine and undergoing a first color change as it becomes progressively wetter with urine, said first color change being both qualitative and quantitative, said core zone including an enzymatic moisture indicator that changes from yellow through light green to deep turquoise;

(B) an inner zone having a urine absorption capacity of 20–100 cc of urine and undergoing a second color change when it becomes saturated with urine, said inner zone including a hydratable salt moisture indicator that changes from a colorless white to blue; and (C) an outer zone having a urine absorption capacity of greater than 100 cc of urine and undergoing a third color change when it becomes saturated with urine, said outer zone including a capillary action moisture indicator that changes from white to red;

said core zone being configured and dimensioned to cover a urethral meatus;

each of said first, second and third color changes being visible at the respective one of said zones, visually distinct, and a function of the quantity of urine absorbed in said one zone;

said pad including a first layer of a wicking material, a second layer of an absorbent material disposed over said first layer, and a third layer of moisture-impervious material disposed over said second layer, said core zone, said inner zone, and said outer zone being in said second layer.

23. The pad of claim 22 wherein said inner zone is concentrically disposed about said core zone, and said outer zone is concentrically disposed about said inner zone.

24. The paid of claim 22 wherein said inner zone is disposed at one end of said core zone, and said outer zone is disposed at the other end of said core zone.

25. The pad of claim 24 wherein said inner zone is disposed at the rear of said core zone, and said outer zone is disposed at the front of said core zone.

26. A confidence pad for a female enabling a quantitative estimate of urinary incontinence, said pad comprising at least two urine absorption zones as follows:

(A) a first zone having a first urine absorption capacity and undergoing a first color change as it becomes progressively wetter with urine; and (B) a second zone having a greater urine absorption capacity than said first urine absorption capacity and undergoing a second color change when it becomes saturated with urine;

said first and second color changes being visible at the respective one of said zones, visual distinct, and a function of the quantity of urine absorbed in said one zone.

27. The pad of claim 1 additionally comprising a layer of wicking material for distributing a urine discharge to said first, second and third zones in predetermined proportions.

28. The pad of claim 1 wherein there is no overflow of urine from said first and second zones to said second and third zones, respectively.

29. The pad of claim 22 wherein there is no overflow of urine from said core and inner zones to said inner and outer zones, respectively.

* * * * *